(12) United States Patent
Vic et al.

(10) Patent No.: US 10,123,962 B2
(45) Date of Patent: Nov. 13, 2018

(54) COSMETIC OR PHARMACEUTICAL COMPOSITION, IN PARTICULAR INTENDED FOR CARE OR FOR MAKEUP

(75) Inventors: Sabine Vic, Semoy (FR); Fabienne Brossard, Orleans (FR); Eric Perrier, Les Cotes d'Arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 13/070,330

(22) Filed: Mar. 23, 2011

(65) Prior Publication Data

US 2011/0243862 A1  Oct. 6, 2011

(30) Foreign Application Priority Data

Mar. 31, 2010 (FR) ...................................... 10 52411

(51) Int. Cl.
| | |
|---|---|
| *A61K 8/88* | (2006.01) |
| *A61K 8/37* | (2006.01) |
| *A61Q 1/06* | (2006.01) |
| *A61K 8/81* | (2006.01) |

(52) U.S. Cl.
CPC .................. *A61K 8/88* (2013.01); *A61K 8/37* (2013.01); *A61K 8/8111* (2013.01); *A61Q 1/06* (2013.01); *A61K 2800/262* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 3,157,681 A | | 11/1964 | Fischer |
| 3,947,571 A | * | 3/1976 | Murphy et al. .................. 424/64 |
| 5,000,937 A | * | 3/1991 | Grollier et al. .................. 424/47 |
| 5,606,015 A | * | 2/1997 | Chiou ...................... C04B 24/26 528/495 |
| 5,843,407 A | * | 12/1998 | El-Nokaly ........... A61K 8/0295 252/299.01 |
| 6,268,466 B1 | | 7/2001 | MacQueen et al. |
| 6,469,131 B2 | * | 10/2002 | Lawson et al. ............... 528/335 |
| 6,503,522 B2 | * | 1/2003 | Lawson ............... A61K 8/0229 424/401 |
| 6,552,160 B2 | | 4/2003 | Pavlin |
| 6,592,857 B2 | | 7/2003 | Lawson et al. |
| 7,112,650 B2 | | 9/2006 | Slany et al. |
| 7,276,547 B2 | | 10/2007 | Pinzon et al. |
| 2003/0223943 A1 | | 12/2003 | Uang et al. |
| 2005/0191327 A1 | | 9/2005 | Yu et al. |
| 2006/0204460 A1 | | 9/2006 | Takeda et al. |
| 2007/0000072 A1 | * | 1/2007 | Aeby ....................... A61K 8/06 8/405 |
| 2007/0041920 A1 | * | 2/2007 | Blin ..................... A61K 8/8111 424/64 |
| 2009/0280077 A1 | * | 11/2009 | Yoshida et al. ................. 424/59 |

FOREIGN PATENT DOCUMENTS

| | | |
|---|---|---|
| EP | 1 279 397 A2 | 1/2003 |
| EP | 1 414 886 A1 | 5/2004 |
| EP | 1 905 411 A1 | 4/2008 |
| EP | 2 156 821 A1 | 2/2010 |
| WO | WO 01/97758 A2 | 12/2001 |

OTHER PUBLICATIONS

Haimalate PAM Product Sheet, May 2011, retrieved online on Jun. 3, 2013, pp. 1-2.*
Definition of Salve, The Free Dictionary, http://www.thefreedictionary.com/p/salve, p. 1-3, retrieved online on Nov. 14, 2013.*
Alzo INternations, Wickenol 171—Ethylhexyl hydroxystearate, retrieved online on Mar. 14, 2016.*
Merriam-Webster, Definition of Alcohol, retrieved online on Mar. 16, 2106.*
Berardesca. "EEMCO guidance for the assessment of stratum corneum hydration: electrical methods." *Skin Research and Tech* vol. 3. 1997. pp. 126-132.
Zinkel et al. "Naval Stores: Production Chemistry Utilization." *Pulp Chemical Associations, Inc. New York*. 1989. pp. 346-349, 846-868.
Arizona Chemical: "Beautiful chemistry—Specialty polymeric gellants for personal care & cosmetics," Jun. 14, 2006 <http://web.archive.org/web/20060614223942/arizonachemical.com/gellants/pdfs/personalcare_cosmetics brochure.pdf> XP7915597.
Dr. K.T. Griffin Lai, "Personal care products formulated with vegetable-based specialty gallant polyamides," *IP.COM Journal*, IP.COM Inc., West Henrietta, NY, US, Apr. 2, 2008. XP13124372.
French Search Report for priority French application No. 1052411 dated Nov. 8, 2010.

* cited by examiner

Primary Examiner — Jennifer A Berrios
(74) Attorney, Agent, or Firm — Merchant & Gould P.C.

(57) ABSTRACT

A composition includes from 40 to 80% by weight of at least one non-volatile hydrogenated polyalkylene oil; from 10 to 50% by weight of at least one tertiary-amide-terminated polyamide (ATPA) polymer; and further at least one fatty acid ester having at least one free hydroxyl group, and preferably a hydroxystearate ester. The composition is translucent.

15 Claims, No Drawings

COSMETIC OR PHARMACEUTICAL COMPOSITION, IN PARTICULAR INTENDED FOR CARE OR FOR MAKEUP

This application claims benefit of Serial No. 1052411 filed 31 Mar. 2010 in France and which application is incorporated herein by reference. A claim of priority, to the extent appropriate is made.

The invention relates to a cosmetic or pharmaceutical composition, in particular intended for care or for makeup, comprising a transparent or translucent base, and optionally coloring agents, to the method for preparing same and to the cosmetic methods using said composition.

PRIOR ART

Polyamide polymers which make it possible to prepare cosmetic compositions, in particular for making up the lips, which are transparent or translucent, are known. These compositions may optionally be colored. Ester-terminated polyamide copolymers (ETPA) or tertiary-amide-terminated polyamide copolymers (ATPA) which make it possible to obtain such compositions are, for example, known.

WO 01/97558 discloses an Ester Terminated PolyAmide (ETPA).

Griffin discloses in *IP.COM JOURNAL* IP.COM INC, West Henrietta, N.Y., US formulae of personal care products cosmetic formulated with gellant polyamides of PAOPA type, marketed by US Company Arizona Chemical under the trade name SYLVA CLEAR®.

US Company Arizona Chemical also markets tertiary-amide-terminated polyamide copolymers (ATPA) under the trade name SYLVA CLEAR®.

Tertiary-amide-terminated polyamide (ATPA) polymers, and the uses thereof in the cosmetics industry, are known in themselves and in particular described in EP 1,279,397; EP 1,414,886 A1; EP 1 905 411; EP 2,156,821; US 2003/0223943; US 2009/0,280,077; U.S. Pat. Nos. 6,469,131, 6,592,857, 6,552,160, 6,268,466 and 6,503,522, the content of which is included in the present invention by way of reference.

Moreover, U.S. Pat. No. 7,276,547 and application US 2005/0191327 each describe a cosmetic composition comprising a fatty liquid phase, a first polymer and a second polymer, for the preparation of anhydrous sticks of the lipstick type. These compositions may be translucent ("Clear") and may comprise various types of compounds by way of fatty liquid phase, for instance liposoluble esters.

However, as indicated in some of their examples, such compositions display a lack of stability, even thought it is acceptable according to the authors, owing to the presence of a film of exudate of compounds of the fatty phase, at the surface of the stick, after keeping at a temperature of 45° C.

In addition, these compositions may have other drawbacks, for example their rigidity, which leads to breaking of the sticks or the loss, over time, of their translucent or transparent nature, which impairs the visual impression, both for the composition itself and for the film, applied for example to the lips, using such a composition.

Furthermore, it is necessary to take into account the preparation of these compositions, which are normally hot-cast and then cooled. The temperature variations may also be responsible for the formation of a cavity within the cooled mass of the composition, or else for variations in the color of the composition, for example linked to a loss of homogeneity related to a "demixing" process.

PURPOSES OF THE INVENTION

The present invention aims to remedy the above-mentioned drawbacks, by providing a composition, especially intended for care or makeup, in particular of the lips.

The present invention aims to provide a cosmetic or pharmaceutical composition intended for moisturizing the lips, the parts of the face and/or the parts of the body to which it is applied.

The purpose of the invention is also to solve the technical problem consisting of the provision of a composition for preparing such a cosmetic or pharmaceutical composition, said composition being transparent, having better brightness and stable at 45° C., i.e. without excessive or substantial exudation of lipophilic compounds through the polymer matrix, in particular when in the form of sticks like lipsticks, or balms notably for the lips.

The purpose of the invention is also to solve these technical problems in a reliable and reproducible manner which can be used on the industrial scale, in particular in the cosmetics industry.

DESCRIPTION OF THE INVENTION

In all the description and claims the percentages are given in weight unless otherwise stated.

Thus, the present invention is directed towards a composition comprising:
  from 40 to 80% by weight of at least one non-volatile hydrogenated polyalkylene oil, and
  from 10 to 50% by weight of at least one tertiary-amide-terminated polyamide (ATPA) polymer, of formula (I) below:

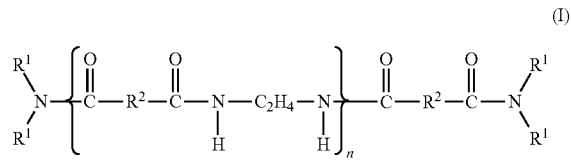

in which
  n is a whole number denoting the number of units present in formula (I), it being possible for n to range from 1 to 10, preferably from 1 to 5,
  the $R^1$ radicals, which may be identical or different, denote a hydrocarbon-based group containing from 1 to 22 carbon atoms,
  the $R^2$ radicals, which may be identical or different at each occurrence, denote a hydrocarbon-based group containing from 2 to 54 carbon atoms, with the proviso that at least 50% of the $R^2$ radicals have from 30 to 42 carbon atoms,
  and further at least one fatty acid ester comprising at least one free hydroxyl group.

According to a particular embodiment, the composition according to the invention advantageously comprises from 5% to 20% by weight of the composition, of fatty acid ester.

According to another particular embodiment, the composition according to the invention advantageously comprises from 15% to 50% by weight, more preferentially from 15% to 30% by weight of the composition, of an ATPA polymer.

According to a further particular embodiment, the composition according to the invention may also comprise one or more fatty alcohols containing from 8 to 30 carbon atoms, which are advantageously solid at room temperature.

A fatty alcohol, which is solid at ambient temperature, which is particularly preferred is cetyl alcohol.

According to an advantageous embodiment, the composition comprises up to 20% by weight, particularly from 1% to 20% by weight, and even more particularly from 1 to 15% by weight of said fatty alcohol.

The presence of the solid fatty alcohol improves the texture, lowers exudation and provides less elasticity, properties which are sought in sticks like lipsticks. The solid fatty alcohol further improves transparency, brightness of the formulation. According to a particular embodiment, it can also be used from 1 to 5% by weight of said solid fatty alcohol.

The composition according to the invention is advantageously substantially anhydrous.

By the term "substantially" it is meant that the composition is completely anhydrous, namely does not contain water, or is free of water, or contains a few percentage of water which does not affect the anhydrous character thereof.

The ATPA polymers in accordance with formula (I) above are, for example, obtained by reacting a whole number x of equivalents of a dimer acid reactant of formula HOOC—$R^2$—COOH, a whole number y of equivalents of ethylenediamine represented by the formula: $NH_2$—$C_2H_4$—$NH_2$ and a whole number z of equivalents of a secondary monoamine reactant of formula $R^1$—NH—$R^1$, the equivalents x, y and z being other than 0.

The number n of units present in formula (I) can range from 1 to 10, preferably from 1 to 5.

According to one preferred form of the invention, the ATPA polymer is a blend of polymers of formula (I) with various values of n of between 1 and 10.

The $R^1$ radicals, which may be identical or different at each occurrence, denote a hydrocarbon-based group containing from 1 to 22 carbon atoms.

The $R^1$ radicals preferably denote alkyl or alkenyl radicals containing from 4 to 22 carbon atoms, for example 8, 10, 12, 14, 16, 18, 20 or 22 carbon atoms.

Preference is given to alkyl groups and also alkenyls having from 1 to 3 unsaturation sites and more preferentially just one unsaturation site.

Preferentially, the $R^1$ radicals containing from 14 to 22 carbon atoms are particularly preferred.

The appropriate $R^1$ groups are introduced into the molecule of formula (I) when a secondary monoamine $R^1$—NH—$R^1$ ($R^1$ being as defined above) is used as coreactant in the preparation of the ATPA polymer of the invention.

Among the secondary monoamines which are commercially available, mention may be made of those originating from various sources, for instance Witco Corporation (Greenwich, CT); Akzo Nobel Chemicals, Surface Chemistry (Chicago, IL), and Aldrich (Milwaukee, WI).

A secondary amine of formula $C_{18}H_{37}$—NH—$C_{18}H_{37}$ or a di($C_{14}$-$C_{18}$)alkylamine mixture is advantageously used.

The $R^2$ radicals are hydrocarbon-based groups containing from 2 to 54 carbon atoms, preferably from 4 to 42 carbon atoms, even more preferentially from 4 to 42 carbon atoms, with the proviso that at least 50% of the $R^2$ groups have from 30 to 42 carbon atoms.

These groups are introduced during the preparation of the ATPA polymer from a polymerized fatty acid, also known as dimer acid, having the formula HOOC—$R^2$—COOH ($R^2$ being as defined above).

The diacid is generally an organic molecule containing two carboxylic acid groups or equivalent reactive groups.

Preferentially, the diacid is a polymerized fatty acid.

The polymerized fatty acid is generally a mixture of structures, in which the dimers individually may be saturated or unsaturated, cyclic or acyclic.

A good description of the polymerization of fatty acids is indicated in particular in U.S. Pat. No. 3,157,681, and in the work *Naval Stores-Production Chemistry and Utilization*, D. F. Zinkel and J. Russel (eds).

Among the dimer acids that are commercially available, mention may, for example, be made of the product sold under the trade name Unydime by the company Union Carbide Corporation (Wayne, N.J.), the dimer acid sold under the trade name Empol by the company Henkel Corporation, Emery Oleochemicals Division (Cincinnati, Ohio), the dimer acid sold under the trade name Pripol by the company Unichema North America (Chicago, Ill.) and the dimer acid sold under the trade name Sylvadym by the company Arizona Chemical division of International Paper (Panama City, Fla.).

The ATPA polymers of the invention contain at least 50% of $R^2$ radicals containing from 30 to 42 carbon atoms.

Preferably, the ATPA polymers contain at least 75% of $R^2$ radicals containing from 30 to 42 carbon atoms, even more preferentially at least 90%.

These ATPA polymers may also comprise $R^2$ groups having less than 30 carbon atoms, for example having from 4 to 19 carbon atoms, more preferentially from 4 to 8 carbon atoms.

The carbon atoms may be arranged in linear, branched or cyclic formation, and an unsaturation may be present between two carbon atoms. $R^2$ may be aliphatic or aromatic. When they are present, these $R^2$ groups with a low carbon number are generally hydrocarbon-based (constituted solely of carbon and hydrogen atoms).

These groups represent less than 50% of the total of the $R^2$ groups, and preferably from 5% to 35% of the total of the $R^2$ groups.

$R^2$ may comprise one or more unsaturations or else be hydrogenated.

According to one particularly preferred embodiment of the invention, the —(CO)—$R^2$—(CO)— group contains 36 carbon atoms, and even more preferentially is a residue of the dimer of linoleic acid, which is hydrogenated or non-hydrogenated.

Advantageously, the ATPA polymer is a polymer of formula (I) as defined above, in which $R^1$ contains from 14 to 22, and in particular from 14 to 18 carbon atoms, n is a whole number that can range from 2 to 5, and $R^2$ contains from 4 to 42 carbon atoms, with the proviso that at least 50% of the $R^2$ groups have from 30 to 42 carbon atoms, $R^2$ being saturated or comprising one or more unsaturations, or any one of the blends of the above-mentioned polymers.

A first preferred ATPA polymer is a copolymer which has the name (INCI) Ethylenediamine/Hydrogenated Dimer Dilinoleate Copolymer bis-di-$C_{14-18}$ Alkyl Amide, which is commercially available.

A second preferred ATPA polymer is a copolymer which has the name (INCI) Bis-Dioctadecylamide Dimer Dilinoleic Acid/Ethylenediamine Copolymer, which is commercially available.

The composition according to the invention may also comprise a blend of ATPA polymers, it being possible for said blend to advantageously comprise at least one preferred copolymer.

The fatty acid ester(s) comprising at least one free hydroxyl group, present in the composition in an amount such that the weight ratio [fatty acid esters]/[ATPA] is included in a range of from 1/4 to 4/1, preferentially included between 1/3 and 3/2.

The fatty acid ester is preferably of the hydroxystearate ester type, and more preferably is ethylhexyl hydroxystearate.

The hydrogenated polyalkylene oil is present in the composition in an amount such that the ratio [hydrogenated polyalkylene]/[ATPA] weight is included in a range of from 5/1 to 3/2, preferentially included between 4/1 and 2/1.

The hydrogenated polyalkylene oil is advantageously hydrogenated polyisobutene.

The composition may also comprise other fatty phase structuring or gelling agents other than the ATPA polymers, and in particular polymers or copolymers which are at least partially soluble or as a dispersion in fatty phases.

Such gelling or structuring agents are, for example, polyamides, such as ester-terminated polyamide copolymers (Uniclear®, Union Carbide), or else silicone polyamides, or alternatively L-glutamide derivatives, such as dibutyl lauroyl glutamide, sold by Ajinomoto, or a mixture thereof, fumed silicas, or alternatively hydrogenated or nonhydrogenated copolymers comprising at least one styrene unit, such as, for example, a hydrogenated styrene/methylstyrene/indene copolymer, which is commercially available.

The composition may also comprise one or more waxes chosen from natural or synthetic waxes.

According to one particular embodiment, the composition advantageously comprises:
  from 15% to 50%, in particular 15 to 30%, by weight of an ATPA polymer of formula (I),
  from 40% to 80% by weight of a hydrogenated polyalkylene,
  from 5% to 20% by weight of ethylhexyl hydroxystearate, and optionally:
  from 0 to 20%, in particular 1 to 20%, and more particularly 1 to 15%, by weight of solid fatty alcohol,
  from 0 to 5% by weight of glutamide-derived gelling agent,
  from 0 to 15% by weight of a styrene copolymer.

According to another particular embodiment, the composition advantageously comprises:
  from 15% to 50%, in particular 15 to 30%, by weight of an ATPA polymer having the name (INCI) Bis-Dioctadecylamide Dimer Dilinoleic Acid/Ethylenediamine Copolymer,
  from 40% to 80% by weight of hydrogenated polyisobutene,
  from 5% to 20% by weight of ethylhexyl hydroxystearate, and optionally:
  from 0 to 20%, in particular 1 to 20%, and more particularly 1 to 15%, by weight of cetyl alcohol,
  from 0 to 5% by weight of a dibutyl lauroyl glutamide mixture,
  from 0 to 15% by weight of a hydrogenated styrene/methylstyrene/indene copolymer.

According to one particularly preferred embodiment, the composition according to the invention is translucent or transparent.

The term "translucent" means "which allows light to pass, without enabling objects to be distinguished".

The term "transparent" means "which allows light to pass and enables objects to be distinguished".

The compositions of the invention make it possible to solve the technical problems stated above.

However, both surprisingly and unexpectedly, the inventors have also demonstrated that the compositions which are the subjects of the invention have a moisturizing effect. In addition to this unexpected moisturizing effect, the film applied to the lips or the skin using the composition of the invention exhibits an excellent staying power. Furthermore, when a film of said composition is applied to the lips as a lipstick base, the film of lipstick applied on top of the base film, regardless of whether or not it is in accordance with the invention, itself exhibits an improved staying power, without migration of the film.

The present invention is therefore particularly suitable for preparing cosmetic or pharmaceutical compositions intended for lip care or making up the lips, but also relates to any cosmetic composition for caring for or making up the face and/or the body, for example the legs, arms, back, armpits, etc.

A subject of the invention is directed towards a cosmetic or pharmaceutical composition, in particular intended for lip care or for making up the lips, comprising up to 100% by weight of the composition as defined above, advantageously from 60% to 100% by weight.

The cosmetic composition is in particular characterized in that it is in the form of a lipstick base or of a care balm, in particular a lip care balm, and in particular a moisturizing balm, advantageously consisting of the composition as defined above.

A "lipstick base" is a composition applied as a film directly to the lips, prior to the application of a film of lipstick.

The lipstick base is in particular aimed at improving the staying power of the film of lipstick, for example by avoiding or slowing down the migration of the compounds of the film of lipstick, in particular pigments, which makes it possible to prolong the aesthetic effect of the makeup.

According to one particularly preferred embodiment, the lipstick base or the lip care balm is transparent but could also be more or less colored.

The use of this cosmetic composition is also possible as a top coat, where the application is done over a lip product, in order to bring emollience, moisturization and/or gloss onto another lip product already present.

Another subject of the invention relates to a cosmetic or pharmaceutical composition as defined above, characterized in that it comprises at least one coloring agent comprising or consisting of at least one pigment, said coloring agent preferably being present at up to 40% by weight of the cosmetic composition, preferably from 5% to 35% by weight.

The coloring agent, which is advantageously in the form of a powder or of a mixture of powders, is more particularly insoluble in the base of the composition.

Said coloring agent advantageously consists of a mixture of powders selected from at least one pigment, at least one filler, and any mixture thereof.

The pigments may be chosen from mineral pigments, organic pigments and pearlescent pigments.

Among the mineral pigments, mention may be made, by way of examples, of titanium dioxide (rutile or anatase), which is optionally surface-treated; black, yellow, red and brown iron oxides; manganese violet; ultramarine blue; chromium oxide; chromium oxide hydrate and ferric blue.

Among the organic pigments, mention may be made, for example, of the pigments D & C red no. 19; D & C red no. 9; D & C red no. 21; D & C orange no. 4; D & C orange no. 5; D & C red no. 27; D & C red no. 13; D & C red no. 7; D & C red no. 6; D & C yellow no. 5; D & C red no. 36; D & C orange no. 10; D & C yellow no. 6; D & C red no. 30; D & C red no. 3; carbon black and lakes based on cochineal carmine.

The pearlescent pigments can be chosen in particular from white pearlescent pigments, such as titanium oxide-coated mica, bismuth oxychloride; and colored pearlescent pigments, such as titanium mica coated with iron oxides, titanium mica coated with ferric blue or chromium oxide, titanium mica coated with an organic pigment of the above-mentioned type, and also pigments based on bismuth oxychloride.

The fillers are chosen in particular from talc, a magnesium silicate hydrate, which is advantageously in the form of particles generally of sizes less than 40 µm; micas of natural origin (for example muscovite, margarite, roscoelite, lipidolite or biotite) or synthetic origin, which are aluminosilicates of varied compositions, advantageously in the form of flakes having sizes of from 2 to 200 µm, preferably from 5 to 70 µm, and a thickness of from 0.1 to 5 µm, preferably from 0.2 to 3 µm; kaolin, an aluminium silicate hydrate, which is advantageously in the form of lamellar particles having sizes of generally less than 30 µm; zinc oxide and titanium oxide; calcium carbonate, advantageously in the form of particles of sizes less than 10 µm, magnesium carbonate and magnesium hydrocarbonate; silica; metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate; these soaps being advantageously in the form of particles of sizes less than 10 µm.

It is also possible to use powders of synthetic polymers which are non-expanded, such as polyethylene, polyesters (for example polyethylene isophthalate or terephthalate), and polyamides (for example nylon); mineral powders such as spherical silica; spherical titanium dioxides; glass and ceramic beads; powders of organic materials of natural origin, for instance crosslinked or noncrosslinked maize, wheat or rice starches; spheronized crosslinked or noncrosslinked, synthetic polymer powders, for instance polyamide powders such as poly-β-alanine powders and nylon powders, polyacrylic acid or polymethacrylic acid powders, divinylbenzene crosslinked polystyrene powders, silicone resin powders and teflon powders.

The coloring agent may constitute up to 40% by weight of the composition according to the invention, preferably from 5% to 35% by weight of the composition.

The compositions as defined above according to the invention may also additionally comprise one or more cosmetic or pharmaceutical active agents advantageously chosen from moisturizing agents or humectants, anti-aging agents, antimicrobial agents, such as farriesol, irgasan (5-chloro-2-(2,4-dichlorophenoxy)phenol), parabens, phenoxyethanol, glycols, synthetic or natural aluminium salts, 4-hydroxybenzoic acid, or a salt or ester thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylene-bis(6-bromo-4-chlorophenol), 3-methyl-4-(1-methylethyl)phenol, 2-benzyl-4-chlorophenol, 3-(4-chlorophenoxy)propanel, 2-diol, 3-iodo-2-propinylbutyl carbamate, chlorhexidine, 3,4,4'-trichlorocarbanilide (TTC), a fragranced antibacterial, thymol, thyme oil, eugenol, clove oil, menthol, mint oil, glycerol monocaprate, glycerol monocaprylate, glycerol monolaurate (GML), diglycerol monocaprate (DMC), salicylic acid N-alkylamides such as, for example, salicylic acid n-octylamide or salicylic acid n-decylamide, etc., or else screening agents which protect against UV radiation, and/or one or more excipients chosen from preservatives, antioxidants, fragrances, surfactants and rheology agents.

According to one variant of the invention, antimicrobial agents such as those mentioned above are combined with preservatives in deodorant compositions.

Another subject of the invention is directed towards a method for preparing a composition as described above, said method comprising a step in which the ATPA polymer or copolymer is dispersed in the fatty acid ester comprising at least one free hydroxyl group, and preferably in an ester of the hydroxystearate ester type, and more preferably in ethylhexyl hydroxystearate.

Another subject of the invention is directed towards a cosmetic care or makeup method characterized in that it comprises the application, to the lips and/or a part of the face and/or of the body, of a film of a cosmetic composition as defined above or prepared according to the method described above, in order to obtain a cosmetic care or makeup effect for the lips and/or a part of the face and/or of the body.

Said method is also characterized in that it comprises the application, to the lips and/or a part of the face and/or of the body, of said cosmetic or pharmaceutical composition in order to obtain a moisturizing film.

According to one preferred variant of said method, the latter is characterized in that it comprises a first step consisting of the application, to the lips, of a film of a lipstick base according to the invention, and then a second step consisting of the application, on top of the first film, of a film of a colored composition for making up the lips, in order to obtain a makeup effect.

The colored composition is then advantageously a colored composition as defined above.

Other purposes, features and advantages of the invention will become clear to those skilled in the art on reading the explanatory description which makes reference to examples that are given only by way of illustration and could not therefore in any way limit the scope of the invention.

The examples are an integral part of the present invention and any feature which appears to be novel over any prior art on the basis of the description taken as a whole, including the examples, is an integral part of the invention with respect to its function and with respect to its generality.

Thus, each example has a general scope.

Furthermore, in the examples, all the percentages are given by weight, unless otherwise indicated, and the temperature is expressed in degrees Celsius unless otherwise indicated, and the pressure is atmospheric pressure, unless otherwise indicated.

EXAMPLES

Example 1

Lipstick Bases

The formulae below are compositions that can be used as lipstick bases. The percentages are expressed by weight of the final composition.

Formula 1

| Phase A | |
|---|---|
| ATPA polymer* | 23.1 |
| Ethylhexyl hydroxystearate | 11.9 |
| Hydrogenated polyisobutene | 60 |
| Phase B | |
| Cetyl alcohol | 5 |

Formula 2

| Phase A | |
|---|---|
| ATPA polymer* | 21.1 |
| Ethylhexyl hydroxystearate | 10.9 |
| Hydrogenated polyisobutene | 56 |
| Phase B | |
| Cetyl alcohol | 2 |
| Hydrogenated styrene/methylstyrene/indene copolymer | 10 |

Formula 3

| Phase A | |
|---|---|
| ATPA polymer* | 16.5 |
| Ethylhexyl hydroxystearate | 8.5 |
| Hydrogenated polyisobutene | 71 |
| Phase B | |
| Cetyl alcohol | 2 |
| Dibutyl lauroyl glutamide | 2 |

*The ATPA polymer is that of which the INCI name = Bis-Dioctadecylamide Dimer Dilinoleic Acid/Ethylenediamine Copolymer Method for Preparing Formulae 1 to 3:

The various components of phase A are melted at 95° C. with stirring (Rayneri TurboTest, 300 rpm).

Phase B is added and the mixture is allowed to melt with stirring.

When the mass is completely homogeneous, it is poured into suitable moulds, and left to cool.

These compositions are transparent and stable at 45° C., i.e. without excessive or substantial exudation of lipophilic compounds through the polymer matrix. They are directly applied to the lips before the application of a film of lipstick. They improve the staying power of the lipstick applied on top of the base.

Furthermore, the translucent or transparent nature of the base does not impair the visual impression of the lipstick applied on top.

These compositions can also be used as a lip care balm.

Example 2

Makeup Composition Comprising a Transparent or Translucent Base

The composition below can be used as a lipstick and comprises the composition according to the invention. The percentages are expressed by weight of the final composition.

Formula 4

| Phase A | |
|---|---|
| ATPA polymer* | 16.5 |
| Ethylhexyl hydroxystearate | 8.5 |
| Hydrogenated polyisobutene | 47.2 |
| Phase B | |
| Cetyl alcohol | 2 |
| Hydrogenated styrene/methylstyrene/indene copolymer | 5 |
| Dibutyl lauroyl glutamide | 2 |
| Phase C | |
| Pigment Yellow 6 Lake | 3.9 |
| Pigment Red 7 | 2.8 |
| Iron oxides | 1.1 |
| Red 6 | 0.9 |
| Titanium dioxide | 0.1 |
| Hydrogenated polyisobutene | 10 |

*The ATPA polymer is that of which the INCI name = Bis-Dioctadecylamide Dimer Dilinoleic Acid/Ethylenediamine Copolymer Method for Preparing the Composition:

The components of phase A are melted at 95° C. with stirring (Rayneri TurboTest, 300 rpm).

Phase B is added and the mixture is allowed to melt with stirring.

The pigments of phase C are ground in the presence of hydrogenated polyisobutene. This phase C is then added to the liquid phase previously prepared.

When the mass is completely homogeneous, it is poured into suitable moulds and allowed to cool.

The colored composition is applied directly to the lips or after the application of a lipstick base. In both cases, it exhibits excellent staying power.

Example 3

Evaluation of the Moisturizing Effect of a Composition According to the Invention Composition Used for the Moisturization Test A composition according to formula 5 below is prepared in accordance with the method described in example 1.

Formula 5

| Phase A | |
|---|---|
| ATPA polymer* | 16.5 |
| Ethylhexyl hydroxystearate | 15.5 |
| Hydrogenated polyisobutene | 46 |
| Phase B | |
| 95% cetyl alcohol | 2 |
| Propylene glycol dibenzoate | 20 |

*The ATPA polymer is that of which the INCI name = Bis-Dioctadecylamide Dimer Dilinoleic Acid/Ethylenediamine Copolymer Materials and Methods Principle of the Measurement The measurement of the electrical properties of the skin is an objective method for evaluating skin moisturization (*Skin Res. Tech.* 1997 (3) 126-132).

The corneometer makes it possible to measure a variation in electrical capacitance linked to the variation in water content of the skin (variation in the dielectric constant of the skin). An electric field is created at the surface of the skin by means of a probe composed of two electrodes. The capacitance of the electrode/skin system is influenced by the changes in dielectric constant of the biological medium in contact with the probe. The measurement thereof thus reflects the state of moisturization of the upper layers of the epidermis.

Equipment

CM825 corneometer from the company Courage & Khazaka

Measurement Time

Before application and 6 hours (after removal of the residual film).

Application Mode

Standardized application (3 vertical passes, 3 horizontal passes) on the forearm. The residual film is removed with absorbent paper before the "6 h after application" measurement.

Statistical Methods

Analysis of variance (ANOVA) using the Statgraphics Plus statistical software (risk α=5%). The mean percentage variation is calculated over all the individuals (n=10).

The significance thresholds are calculated on the moisturization values after 6 hours, as variation relative to before treatment. The p* for the time before treatment is calculated on the crude values.

Results

Table 1 below reproduces the results obtained on the basis of the mean of the data measured.

TABLE 1

|  | Before | 6 hours |
|---|---|---|
| Untreated control | 29.1 | 30.4 |
| Formula 5 | 27.7 | 42.1 |
| p* = | NS | S(p < 0.01) |

*p expresses the significance of the test (p value).
S = significant;
NS = not significant Conclusions Six hours after application of a film of the composition tested on the skin, a significant increase, by a percentage of +46%, in the skin moisturization is observed at the level of the site of application, compared with the moisturization measured before application of the film.

The composition tested (formula 5) exhibits a significant moisturizing effect at 6 hours compared with the untreated control. This surprising moisturizing effect can be taken advantage of in the context of lip care compositions, for example as a moisturizing balm, or of makeup compositions having an additional moisturizing effect.

Comparative Example 4

Lipstick Composition Base

Comparative Formula 1 Base

| ATPA Polymer* | 19.8 |
|---|---|
| Ethylhexyl Hydroxystéarate | 10.2 |
| Polyisobutène hydrogéné | 10 |
| Polybutène | 60 |

This base, which does not contain a fatty alcohol, solid at ambient temperature, in particular cetyl alcohol, contrary to formulae 1 to 5, has a very cohesive and stretchy structure, thereby having texture features less satisfactory for making a Lipstick or a balm, notably for the care of the lips.

What is claimed is:

1. A transparent lipstick composition with good texture, low exudation and low elasticity consisting of:
   from 50% to 75% by weight of at least one non-volatile hydrogenated polyalkylene oil comprising hydrogenated polyisobutene;
   from 15% to 50% by weight of at least one tertiary-amide-terminated polyamide (ATPA) polymer comprising bis-dioctadecylamide dimer dilinoleic acid/ethylenediamine copolymer;
   from 5% to 20% by weight of ethylhexyl hydroxystearate;
   from 1% to 5% by weight of cetyl alcohol;
   from 0% to 5% by weight of dibutyl lauroyl glutamide gelling agent;
   from 0% to 15% styrene copolymer;
   an antimicrobial agent; and
   from 0% to 40% coloring agent;
   wherein all fatty alcohols present in the lipstick composition are solid at room temperature; and wherein the antimicrobial agents are selected from: parabens, phenoxyethanol, synthetic or natural aluminium salts, 4-hydroxybenzoic acid or a salt or ester thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylene-bis(6-bromo-4-chlorophenol), 3-methyl-4-(1-methylethyl) phenol, 2-benzyl-4-chlorophenol, 3-(4-chlorophenoxy) propanel,2-diol, 3-iodo-2-propinylbutyl carbamate, chlorhexidine, 3,4,4'-trichlorocarbanflide (TTC), and salicylic acid N-alkylamides.

2. The lipstick composition of claim 1, consists of 15% to 30% by weight of the composition of said ATPA polymer.

3. The lipstick composition of claim 1, wherein the ATPA polymer further comprises Ethylenediamine/Hydrogenated Dimer Dilinoleate Copolymer bis-Di-$C_{14-18}$ Alkyl Amide.

4. The lipstick composition of claim 1, wherein an ethylhexyl hydroxystearate/ATPA weight ratio is in a range of from 1/4 to 4/1.

5. The lipstick composition of claim 1, wherein the non-volatile hydrogenated polyalkylene oil consists of hydrogenated polyisobutene.

6. The lipstick composition of claim 1, wherein the non-volatile hydrogenated polyalkylene oil is present in the composition in an amount such that a [hydrogenated polyalkylene oil]/[ATPA] weight ratio is in a range of from 5/1 to 3/2.

7. The lipstick composition of claim 1, wherein:
   bis-dioctadecylamide dimer dilinoleic acid/ethylenediamine copolymer is from 15% to 50% by weight of the lipstick,
   ethylhexyl hydroxystearate is from 5% to 20% by weight of the lipstick.

8. The lipstick composition of claim 1,
   wherein:
   dibutyl lauroyl glutamide is from 1% to 3% by weight of the lipstick, and
   the styrene copolymer is a hydrogenated styrene/methylstyrene/indene copolymer in an amount from 0% to 10% by weight of the lipstick.

9. The lipstick composition of claim 1, in the form of a transparent lip care balm.

10. The lipstick composition of claim 1, wherein the one coloring agent comprises at least one pigment.

11. The lipstick composition of claim 10, wherein said coloring agent ranges from 10% to 35% by weight of the composition.

12. The lipstick composition of claim 10, wherein the coloring agent consists of a mixture of powders selected from at least one pigment, at least one filler, and any mixture thereof.

13. The lipstick composition of claim 10, wherein the pigment is selected from a mineral pigment, an organic pigment and a pearlescent pigment.

14. The lipstick composition of claim 1, in the form of a transparent moisturizing balm.

15. The lipstick composition of claim 1, wherein the dibutyl lauroyl glutamide gelling agent is present from 1% to 3% by weight, and the styrene copolymer is present from 0% to 10% by weight.

* * * * *